United States Patent [19]
Noble

[11] Patent Number: 5,403,290
[45] Date of Patent: Apr. 4, 1995

[54] GASTRIC ADAPTER/STOPCOCK

[76] Inventor: Lisa W. Noble, 5656 Coralite St., Long Beach, Calif. 90808

[21] Appl. No.: 870,814

[22] Filed: Apr. 20, 1992

[51] Int. Cl.⁶ .............................................. A61M 5/00
[52] U.S. Cl. ..................................... 604/248; 604/905; 137/625.47
[58] Field of Search ................. 604/247, 248, 905, 32; 137/625.47, 625.41; 251/148, 150; 285/332, 80

[56]  References Cited
U.S. PATENT DOCUMENTS

| | | |
|---|---|---|
| 628,907 | 7/1899 | Hart . |
| 3,185,179 | 5/1965 | Harautuneian . |
| 3,678,960 | 7/1972 | Leibinsohn . |
| 3,783,900 | 1/1974 | Waldbillig . |
| 3,788,602 | 1/1974 | Kitzie . |
| 3,834,372 | 9/1976 | Turney ........................ 137/625.47 |
| 3,957,082 | 5/1976 | Fuson et al. . |
| 4,219,021 | 8/1980 | Fink . |
| 4,253,684 | 3/1981 | Tolbert et al. ........................ 604/905 |
| 4,511,163 | 4/1985 | Harris et al. ........................ 604/905 |
| 4,566,480 | 1/1986 | Parham ........................ 137/625.47 |
| 4,593,717 | 6/1986 | Levasseur . |
| 4,604,093 | 8/1986 | Brown et al. . |
| 4,692,150 | 9/1987 | Cianci et al. ........................ 604/905 |
| 4,838,855 | 6/1989 | Lynn ........................ 604/248 |
| 4,950,230 | 8/1990 | Kendell ........................ 604/248 |
| 4,967,743 | 11/1990 | Lambert ........................ 604/905 |
| 4,967,797 | 11/1990 | Manska . |
| 5,074,334 | 12/1991 | Onodera ........................ 604/248 |
| 5,078,688 | 1/1992 | Lobodzinski et al. ........................ 604/248 |
| 5,135,026 | 8/1992 | Manska ........................ 604/248 |

OTHER PUBLICATIONS

Sales Brochure, USCI, A Division of C.R. Bard, Inc., Billerica, Mass. 01821, Jun. 1974.

Primary Examiner—C. Fred Rosenbaum
Assistant Examiner—Chalin Smith
Attorney, Agent, or Firm—William L. Klima

[57]  ABSTRACT

A gastric adapter comprising a three-way stopcock. The stopcock includes connectors having tapered surfaces for sealing tightly with the ends of nasogastric, gastrostomy and feeding tubing and includes fluid passageways of sufficient diameter so as to be capable of conveying viscous fluids such as emulsion, suspensions and slurrys to provide effective operation and use in the particular environment of administering critical fluids and medications through nasogastric and gastrostomy tubing.

16 Claims, 1 Drawing Sheet

GASTRIC ADAPTER/STOPCOCK

BACKGROUND OF THE INVENTION

This invention relates to an improved gastric adapter comprising a three-way stopcock for use with nasogastric and gastrostomy tubes. The device maintains a closed, contamination-free system while providing easy access for instilling hydration, medication, continuous feedings and gastric residual checks.

PRIOR ART

Currently, the method used for interrupting the backflow of gastric secretions through nasogastric and gastrostomy tubing during delivery of fluids to a patient is to use a thumb and forefinger "pinch" to occlude the tubing. This current ineffective method frustrates the health care practitioner as it becomes difficult to manually "pinch off" the tubing while attempting to infuse critical fluids and medications. Inevitably, secretions erupt from the end of the tube spilling onto the patient, bed and practitioner during use.

Three-way stopcock valves are readily available with their operation well known in the art for use in administrating I.V. fluids and medications. These stopcocks typically employ means for selectively coupling two or three of the three or more fluid passageways entering into the stopcock device. These devices provide the advantage of selectively adding one or more fluids simultaneously along a feed passageway to the patient.

However, these prior art devices are not suitable for use with nasogastric and gastrostomy tubes. For example, either the tubing connections of these prior art stopcock devices are inappropriate or incompatible for leakage-proof connections with these type of tubes and/or the fluid passageways through these devices are too small to accommodate the viscous fluids (e.g. emulsions, suspensions and slurrys) associated with use of nasogastric and gastrostomy tubes.

SUMMARY OF THE INVENTION

An object of the present invention is to provide an improved stopcock device.

Another object of the present invention is to provide an improved stopcock device for use with nasogastric and gastrostomy tubes.

A further object of the present invention is to provide an improved stopcock device constructed for improving the administration of various fluids and medications associated with nasogastric and gastrostomy treatment.

A still further object of the present invention is to provide a stopcock device including an elongated body member having a tapering extension constructed for tightly sealing with the ends of nasogastric and gastrostomy tubes, the elongated body having a substantially round opening leading to a cavity disposed therein, the tapering extension having a first fluid passageway extending therethrough into said cavity; a tapered tubing section constructed for tightly sealing with the end of feeding tubing, the tapered tubing section extending from said elongated body member in a direction substantially opposite to the tapering extension, the tapered tubing section having a second fluid passageway extending therethrough into the cavity, the first fluid passageway positioned at approximately 180 degrees relative to the second fluid passageway; a syringe port extending from the elongated body member and positioned between the tapering extension and the tapered tubing section, the syringe port having a third fluid passageway extending therethrough into the cavity, the third fluid passageway positioned at approximately 90 degrees relative to both the first and second fluid passageways; and a key member including a body portion with a handle, the body portion is disposed within the cavity of the elongated body member when the stopcock is assembled, the body portion having a T-shaped fluid passageway extending therethrough in a plane of rotation of the key member, the T-shaped passageway through the body portion selectively cooperating with the first, second and third fluid passageways for different modes of operation, wherein the diameters of the first and second fluid passageways are selected to accommodate substantially viscous fluids.

A still further object of the present invention is to provide an improved stopcock including an elongated body member having a substantially cylindrical shaped portion connected to a tapering extension, the cylindrical shaped portion having a round opening leading to a cylindrical cavity disposed within the body member with an inner surface of the cavity adjacent the round opening having a circumferential groove disposed therein, the tapering extension having a first fluid passageway extending therethrough into the cylindrical cavity of the elongated body; a tapered tubing section extending from the cylindrical shaped portion of the elongated body member at a position opposite to the tapering extension, the tapering tubing section having a second fluid passageway extending therethrough into the cylindrical cavity of the elongated body member, the first fluid passageway positioned about approximately 180 degrees relative to the second fluid passageway; a syringe port extending from the cylindrical shaped portion of the elongated body member and positioned between the tapering extension and the tapered tubing section, the syringe port having a third fluid passageway extending therethrough into the cylindrical cavity of the elongated body, the third fluid passageway positioned about approximately 90 degrees relative to both the first and second fluid passageways; and a key member including a cylindrical body portion and a handle, the cylindrical body portion is disposed within the cylindrical cavity of the elongated body member when the stopcock is assembled, the cylindrical body portion having a T-shaped fluid passageway extending therethrough in a plane of rotation of the key member with the T-shaped passageway through the cylindrical body portion selectively cooperating with the first, second and third fluid passageways for different modes of operation, the cylindrical body portion having an outer surface provided with a circumferential ridge aligned with the circumferential groove in the surface of the cylindrical cavity in the elongated body member.

DETAILED DESCRIPTION OF PREFERRED EMBODIMENTS

Figure 1:
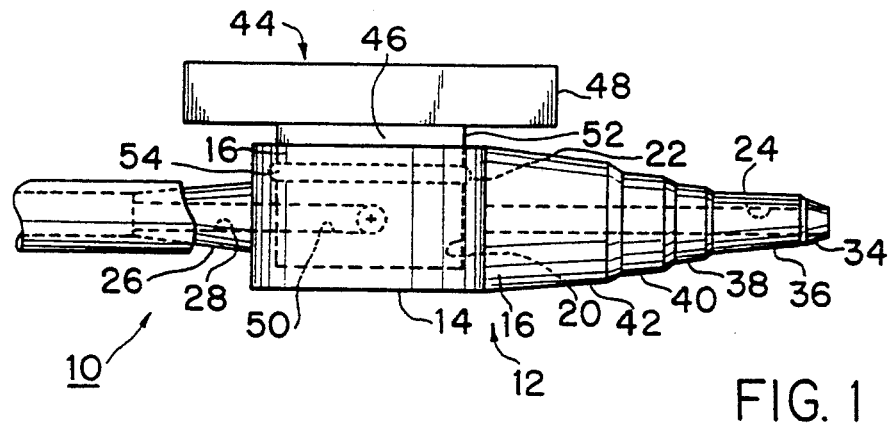
FIG. 1 is a side elevational view of an embodiment of the stopcock according to the present invention.
Figure 2:
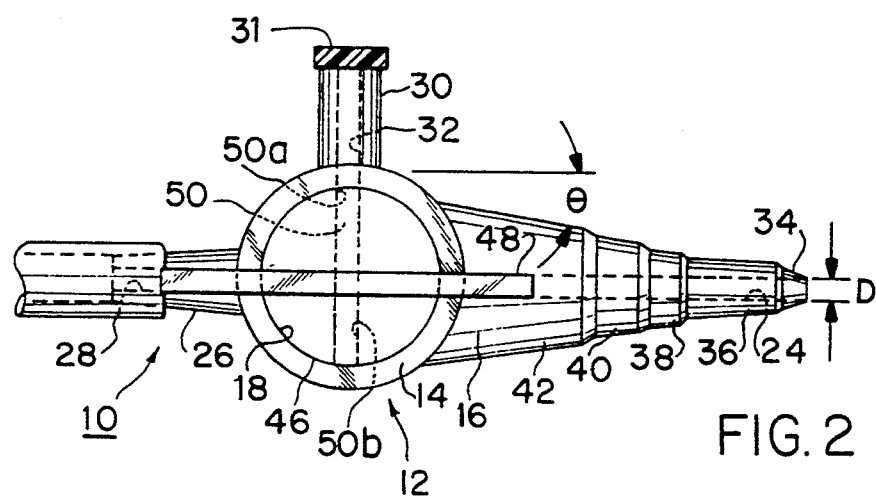
FIG. 2 is a top plan view of an embodiment of the stopcock according to the present invention.

An embodiment of the stopcock 10 according to the present invention is shown in FIGS. 1 and 2. The stopcock 10 comprises an elongated body member 12 defined by a substantially cylindrical shaped portion 14 connected to a tapering extension 16.

The cylindrical shaped portion 14 is provided with a round opening 18 leading to a cylindrical cavity 20. The inner surface of the cylindrical cavity 20 positioned adjacent to the round opening 18 is provided with a circumferential groove 22 disposed in the inner surface thereof.

The tapering extension 16 is provided with a fluid passageway 24 extending therethrough and leading into the cylindrical cavity 20 of the elongated body member 12. A tapered tubing section 26 extends from the cylindrical shaped portion 14 of the elongated body member 12 in a direction opposite to or 180 degrees relative to the tapering extension 16. The tapered tubing section 26 is provided with a fluid passageway 28 leading into the cylindrical cavity 20. A syringe port 30 extends from the cylindrical shaped portion 14 and is located at a position between the tapering extension 16 and tapered tubing section 26 (i.e., 90 degrees relative thereto). The syringe port 30 having a septum 31 is provided with a fluid passageway 32 leading into the cylindrical cavity 20.

The tapering extension 16 is provided with a plurality of different diameter outer circumferential tapered surface portions 34, 36, 38, 40, 42. These various circumferential tapered surface portions can accommodate various sized nasogastric and gastrostomy tubing. The tapering extension 16 and tapered tubing section 26 have tapered surface angles (angle O) in the range of 2.0 to 20 degrees to form tight seals with the inner surface ends of nasogastric, gastrostomy and feeding tubing.

A key member 44 comprising a cylindrical body member 46 is connected to a handle 48. In the embodiment shown, the handle 48 is a substantially rectangular shaped plate member connected on its edge to the cylindrical body member 46. The cylindrical body member 46 is provided with a T-shaped fluid passageway 50 located in a plane of rotation of the cylindrical body member 46 that aligns with the plane in which the fluid passageways 24, 28, 32 are disposed. The individual passageways 50a, 50b, 50c of the T-shaped fluid passageway 50 align and are placed in fluid communication with the various fluid passageways providing different modes of operations of the stopcock 10. The outer peripheral surface 52 of the cylindrical body member 46 is provided with a circumferential ridge 54 aligned with the circumferential groove 22 of the cylindrical cavity.

The cylindrical body member 46 of the key member 44 is then inserted into the cylindrical cavity 20 of the elongated body member 12 while the ridge seal 54 is forced along the inner wall of the cylindrical cavity 20, and subsequently received within the circumferential groove 22 of the cylindrical cavity 20. The ridge seal 54 locks the key member within the elongated body member 12 during its operational life.

The fluid passageways 24 and 28 through the tapering extension 16 and tapered tubing section 26, respectively, have diameters selected for accommodating substantially viscous fluids such as suspensions, emulsions or slurrys therethrough. Many of the medicinal fluids are substantially viscous and must pass through these passageways to be effective during operation. These fluid passageways have diameters in the range of 1.0 millimeters to 5.0 millimeters, preferably 2.5 millimeters. Further, the tapered surfaces 34,36,38,40,42 of the tapering extension 16 and the tapered surface of the tubing section 26 are selected specifically to provide a tight sealing engagement with the inner surfaces of various size tubing. Specifically, a tapering angle O in the range of 2.0 to 20 degrees is utilized.

The stopcock 10 is preferably made of plastic materials to reduce cost of assembly and increase the sanitary applicability of the device. Many surgical grade plastics are available and suitable for this purpose. For example, polycarbonate, polyacetal and polychloroether plastics are suitable for construction of the device according to the present invention.

OPERATION

Figure 3:
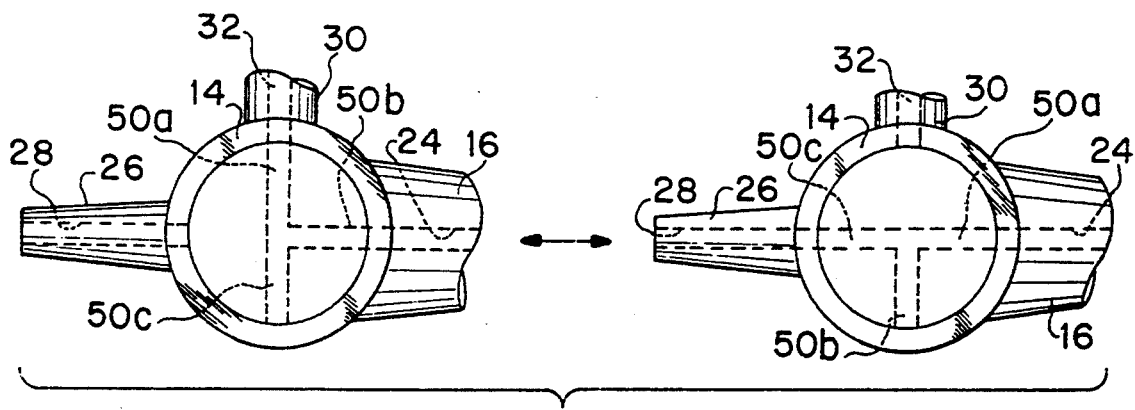
FIG. 3 is a diagram illustrating the sequential operation of the stopcock shown in FIGS. 1 and 2.

The operation of the device according to the present invention will be described referring to FIG. 3. Prior to operation during assembly of the device with various tubing, the handle 48 is located in the position I (i.e., aligned with fluid passageways 24, 28). In this mode of operation, fluid is delivered along the fluid passageways 24 and 28 placed in communication with each other to allow continuous infusion of fluid through passageways 24,28 while preventing the unintended addition of medicine through syringe port 30.

Upon rotating the handle 48 ninety degrees (90° in the counterclockwise direction to position II, passageways of the T-shaped passageway 50 of the key member 44 align with fluid passageways 24 and 32 to allow the addition of medicine through syringe port 30 into passageway 32 now in communication with passageway 24.

The features of the stop cock of the present invention substantially improve the efficiency and operation of a stopcock device. Specifically, the elongated body 12 is of such a shape that a user can securely grip the elongated body member 12 within the hand to allow the precise and easy rotation of the key member 44 during operational mode changes. This is important so as not to disturb the various tubing connections to the stopcock device or the tubing connections to the patient or other medical equipment.

Further, the tapered surfaces of the tapering extension 16 and tapered tubing section 26 accommodate various size tubing and tightly secure these tubing extensions of the stopcock device to the various tubing of the system. This is an important feature to prevent leakage of fluids to and from the body of the patient to prevent contamination and maintain a high level of sterile conditions and applications. Further, these connections are subject to some stress during rotation of the key member 44 relative to the elongated 12 during operational mode changes. These features together provide a highly effective and desirable device for use in this particular application.

EXAMPLE

A suspension of Tylenol, Zantac, Caratate, Dilantin, Decadron or cardiac medicines such as Kapatin, Inderol, Vasotec can be administered with an embodiment of the device as described in detail above.

For example, three or four dry tablets can be crushed into a powder with a mortar and pestle. This powder can be transferred to a 30 cc medicine cup and can be mixed with a little water by drawing up the mixture with a syringe and injecting it through the syringe port section of the device according to the present invention for administering the same to a patient.

DRAWING CHART

10—stopcock
12—elongated body member
14—cylindrical shaped portion
16—tapering extension
20—cylindrical cavity
22—circumferential groove
24—fluid passageway
26—tapered tubing section
28—fluid passageway
30—syringe port
32—fluid passageway
34—circumferential tapered surface portion
36—circumferential tapered surface portion
38—circumferential tapered surface portion
40—circumferential tapered surface portion
42—circumferential tapered surface portion
44—key member
46—cylindrical body number
48—handle
50—T-shaped fluid passageways
50a—individual fluid passageway
50b—individual fluid passageway
50c—individual fluid passageway
52—outer peripheral surface
54—circumferential ridge

I claim:

1. A stopcock, comprising:
an elongated body member defined by a substantially cylindrical body portion and a tapering body portion, said cylindrical body portion having a round opening on one side extending into a cylindrical cavity;
a first tapering tubing connection extending from said tapering body portion, said tapering tubing connection having a first fluid passageway extending therethrough and into said cylindrical cavity;
a second tapering tubing connection extending from said cylindrical body portion of said elongated body member in a direction substantially opposite to said first tapering tubing connection, said second tapering tubing connection having a second fluid passageway extending therethrough and into said cylindrical cavity of said elongated body member, said second fluid passageway is substantially aligned with said first fluid passageway in said first tapering tubing connection;
a syringe port extending from said cylindrical body portion of said elongated body member and positioned between said first tapering tubing connection and said second tapering tubing connection, said syringe port having a third fluid passageway extending therethrough and into said cylindrical cavity of said elongated body member, said third fluid passageway positioned approximately 90 degrees relative to both said first and second fluid passageways; and
a key member defined by a cylindrical body portion and a handle, said cylindrical body portion is disposed within said cylindrical cavity of said elongated body member when said stopcock device is assembled, said cylindrical body portion having a T-shaped fluid passageway extending therethrough in a plane of rotation of said key member, said T-shaped passageway through said cylindrical body portion selectively cooperating with said first, second and third fluid passageways for different modes of operation, said cylindrical body portion having an outer surface provided with a circumferential ridge aligned and fluidly sealing with said circumferential groove in the surface of said cylindrical cavity in said elongated body member.

2. A device according to claim 1, wherein said first and second fluid passageways have diameters selected for conveying substantially viscous fluids such as emulsions, suspensions and slurrys.

3. A device according to claim 2, wherein said diameters of said first and second fluid passageways are in the range of 1.0 to 5.0 millimeters.

4. A device according to claim 3, wherein said tapering body portion is provided with at least one tapering outer surface portion having a tapering ration of 0.01 to 0.30 to form a substantially tight seal with an end of a nasogastric and gastrostomy tubing.

5. A device according to claim 3, wherein said second tapering tubing connection is provided with at least one tapering outer surface portion having a tapering ratio of 0.01 to 0.30 to form a substantially tight seal with an end of feeding tubing or a plastic plug.

6. A device according to claim 4, wherein said second tapering tubing connection is provided with at least one tapering outer surface portion having a tapering ratio of 0.01 to 0.30 to form a substantially tight seal with an end of feeding tubing or a plastic plug.

7. A device according to claim 1, wherein said handle is defined by an elongated rectangular plate member connected on edge to an upper portion of said cylindrical body portion of said key member.

8. A device according to claim 7, wherein said handle is substantially aligned with said tapering body portion when said stopcock is in a closed position with said third fluid passageway of said syringe port being in fluid communication with said first fluid passageway of said tapering extension of said elongated body member.

9. A device according to claim 1, wherein said tapering body portion is provided with multiple outer tapering surface portions of different diameters to accommodate various size nasogastric and gastrostomy tubing.

10. A device according to claim 9, wherein said tapering body portion is provided with four outer tapering surface portions of different diameter to accommodate various size nasogastric and gastrostomy tubing.

11. A gastric adapter, comprising:
an elongated body member defined by a tapering body portion configured for tightly sealing with ends of nasogastric or gastrostomy tubing, said elongated body member having a substantially round opening extending into a cavity disposed in said elongated body member, said tapering body portion having a first fluid passageway extending therethrough and into said cavity;
a tapering tubing connection configured for tightly sealing with an end of a feeding tubing, said tapered tubing connection extending from said elongated body member in a direction substantially opposite to said tapering body portion, said tapering tubing connection having a second fluid passageway extending therethrough and into said cavity of said elongated body member;
a syringe port extending from said elongated body member and positioned between said tapering extension and said tapering tubing connection, said syringe port having a third fluid passageway extending therethrough and into said cavity in said elongated body member, said third fluid passageway positioned at approximately 90 degrees relative to both said first and second fluid passageways; and a key member defined by a body portion with a handle, said body portion is disposed within said cavity of said elongated body member when said stopcock is assemblyed, said body portion having a T-shaped fluid passageway extending therethrough in a plane of rotation of said key member, said T-shaped passageway through said body portion selectively cooperating with said first, second and third fluid passageways for different modes of operation, said first and second fluid passageways have diameters selected to accommodate substantially viscous fluids such as suspensions, emulsions and slurrys.

12. A device according to claim 11, wherein said diameters of said first and second fluid passageways are in the range of 1.0 to 5.0 millimeters.

13. A device according to claim 11, wherein said tapering body portion has a tapering ratio of 0.01 to 0.30.

14. A device according to claim 12, wherein said tapering tubing connection has a tapering ration of 0.01 to 0.30.

15. A device according to claim 13, wherein said tapering tubing connection has a tapering ratio of 0.01 to 0.03.

16. A device according to claim 15, wherein said diameters of said first and second fluid passageways are in the range of 1.0 to 5.0 millimeters.

* * * * *